(12) United States Patent
Steinle et al.

(10) Patent No.: US 11,284,964 B2
(45) Date of Patent: Mar. 29, 2022

(54) MOIRÉ MARKER DEVICE FOR MEDICAL NAVIGATION

(71) Applicant: Brainlab AG, Munich (DE)

(72) Inventors: Wolfgang Steinle, Munich (DE); Timo Neubauer, Grasbrunn-Neukeferloh (DE); Ingmar Hook, Feldkirchen (DE)

(73) Assignee: Brainlab AG, Munich (DE)

(*) Notice: Subject to any disclaimer, the term of this patent is extended or adjusted under 35 U.S.C. 154(b) by 1233 days.

(21) Appl. No.: 14/907,756

(22) PCT Filed: May 28, 2014

(86) PCT No.: PCT/EP2014/061094
§ 371 (c)(1),
(2) Date: Jan. 26, 2016

(87) PCT Pub. No.: WO2015/022100
PCT Pub. Date: Feb. 19, 2015

(65) Prior Publication Data
US 2016/0175064 A1    Jun. 23, 2016

(30) Foreign Application Priority Data

Aug. 13, 2013   (WO) ................ PCT/EP2013/066867
Dec. 13, 2013   (WO) ................ PCT/EP2013/076537

(51) Int. Cl.
*A61B 90/00*     (2016.01)
*G02B 27/60*     (2006.01)
*A61B 34/20*     (2016.01)

(52) U.S. Cl.
CPC .............. *A61B 90/39* (2016.02); *G02B 27/60* (2013.01); *A61B 2034/2055* (2016.02);
(Continued)

(58) Field of Classification Search
None
See application file for complete search history.

(56) References Cited

U.S. PATENT DOCUMENTS 3,572,942 A * 3/1971 teKronnie ................ G01C 5/00
                                                    356/154
5,936,723 A   8/1999 Schmidt et al.
(Continued)

FOREIGN PATENT DOCUMENTS

DE    19639615 C2   10/1999
DE    10045376      4/2002
(Continued)

OTHER PUBLICATIONS

European Patent Office, Written Opinion and Search report for PCT/EP2013/066867, dated Apr. 7, 2014, pp. 9.
(Continued)

*Primary Examiner* — Pascal M Bui Pho
*Assistant Examiner* — Farouk A Bruce
(74) *Attorney, Agent, or Firm* — Tucker Ellis LLP (57) ABSTRACT

The invention relates to a medical navigation marker device (1; 2; 3) comprising a light reflector, characterised in that the reflector features a marker pattern (11, 12, 13; 11, 12, 13, 14, 15, 16; 27, 28; 34, 37; 35, 37) having the following features:—the marker pattern (11, 12, 13; 11, 12, 13, 14, 15, 16; 27, 28; 34, 37; 35, 37) points in more than one spatial direction; —the marker pattern (11, 12, 13; 11, 12, 13, 14, 15, 16; 27, 28; 34, 37; 35, 37) comprises at least one moire pattern (11, 12, 13; 27; 37) which points in more than one spatial direction; and—the marker pattern (11, 12, 13; 11, 12, 13, 14, 15, 16; 27, 28; 34, 37; 35, 37) comprises a face identification pattern (14, 15, 16; 25, 26; 34; 35) which identifies the face of the marker being viewed from a particular spatial direction. The invention also relates to a combination of a medical marker device (1; 2; 3) and a medical navigation system (43) which uses the marker device (1; 2; 3) as a spatial position and/or orientation marker, and to the use of a medical marker device (1; 2; 3)

(Continued)

for providing guidance to a user of a medical navigation system (43) by evaluating the spatial position and/or orientation information provided by the marker device.

12 Claims, 4 Drawing Sheets

(52) U.S. Cl.
CPC .............. *A61B 2034/2057* (2016.02); *A61B 2034/2065* (2016.02); *A61B 2034/2068* (2016.02); *A61B 2090/373* (2016.02); *A61B 2090/3937* (2016.02); *A61B 2090/3983* (2016.02)

(56) References Cited

U.S. PATENT DOCUMENTS

| | | | |
|---|---|---|---|
| 6,384,908 B1 | 5/2002 | Schmidt et al. | |
| 8,059,267 B2 | 11/2011 | Armstrong | |
| 2004/0002642 A1* | 1/2004 | Dekel | G06K 9/3216 600/407 |
| 2004/0233461 A1 | 11/2004 | Armstrong et al. | |
| 2005/0049486 A1 | 3/2005 | Urquhart | |
| 2005/0109855 A1* | 5/2005 | McCombs | A61B 90/36 236/100 |
| 2005/0234332 A1 | 10/2005 | Murphy | |
| 2006/0200025 A1 | 9/2006 | Elliott et al. | |
| 2007/0161888 A1 | 7/2007 | Sherman | |
| 2007/0167703 A1 | 7/2007 | Sherman | |
| 2007/0167741 A1 | 7/2007 | Sherman | |
| 2007/0258560 A1 | 11/2007 | Armstrong et al. | |
| 2007/0280508 A1* | 12/2007 | Ernst | A61B 5/055 382/107 |
| 2008/0045972 A1 | 2/2008 | Wagner | |
| 2008/0071195 A1 | 3/2008 | Cuellar | |
| 2008/0262473 A1* | 10/2008 | Kornblau | A61B 5/06 604/529 |
| 2010/0100081 A1 | 4/2010 | Tuma et al. | |
| 2011/0285987 A1* | 11/2011 | Surrel | G01B 11/2527 356/237.2 |
| 2011/0286010 A1* | 11/2011 | Kusik | G01D 5/34 356/614 |
| 2012/0059244 A1* | 3/2012 | McClelland | A61B 6/12 600/414 |
| 2012/0123299 A1 | 5/2012 | Neubauer | |
| 2013/0218142 A1 | 8/2013 | Tuma et al. | |
| 2014/0114179 A1 | 4/2014 | Müller | |
| 2015/0057756 A1 | 2/2015 | Lang et al. | |
| 2017/0281297 A1 | 10/2017 | Tuma et al. | |

FOREIGN PATENT DOCUMENTS

| | | |
|---|---|---|
| DE | 10045376 A1 | 4/2002 |
| EP | 2179703 B1 | 3/2017 |
| WO | 9938449 | 8/1999 |
| WO | 00/48507 A1 | 8/2000 |
| WO | 0072047 | 11/2000 |
| WO | 0072047 A1 | 11/2000 |
| WO | 2006131373 | 12/2006 |
| WO | 2006131373 A2 | 12/2006 |
| WO | 2007051304 A1 | 5/2007 |
| WO | 2008056180 | 5/2008 |
| WO | 2008056180 A2 | 5/2008 |
| WO | 2009059434 | 5/2009 |
| WO | 2009059434 A1 | 5/2009 |
| WO | 2011012169 | 2/2011 |
| WO | 2011012169 A1 | 2/2011 |
| WO | 2011020505 A1 | 2/2011 |
| WO | 2011047467 | 4/2011 |
| WO | 2011047467 A1 | 4/2011 |
| WO | 2013052187 A2 | 4/2013 |
| WO | 2013053398 A1 | 4/2013 |

OTHER PUBLICATIONS

European Patent Office, Written Opinion and Search report for PCT/EP2014/061094, dated Sep. 23, 2014, pp. 14.
PCT/EP2014/061094 International Search Report dated Sep. 23, 2014.
PCT/EP2013/066867 International Search Report dated Apr. 7, 2014.
Non-Final Office Action for related U.S. Appl. No. 14/907,340, dated Jun. 26, 2019.

* cited by examiner

MOIRÉ MARKER DEVICE FOR MEDICAL NAVIGATION

RELATED APPLICATION DATA

This application is a national phase application of International Application No. PCT/EP2014/061094 filed May 28, 2014, published in the English language, which claims priority to International Application No. PCT/EP2013/066867 filed on Aug. 13, 2013, and International Application No. PCT/EP2013/076537 filed on Dec. 13, 2013, which are hereby incorporated herein by reference.

The present invention relates to a medical navigation marker device which is in particular to be detected by a navigation system in a navigated medical procedure.

Medical marker devices and their use within the environment of a medical navigation system are known for example from DE 196 39 615 C2 which describes reflective marker spheres to be arranged in arrays which exhibit a characteristic arrangement. Another marker device which also uses an arrangement of markers, but in which a plurality of individual marker elements are in turn divided into multiple optical elements, is known from WO 2007/051304 A1. Targets comprising moiré patterns are described in a non-medical motion tracking environment in US 2011/0286010 A1.

In navigated or "image-guided" medical procedures, highly accurate instrument tracking is of utmost importance. This level of accuracy is however directly dependent on the design of the marker, which can significantly influence the accuracy with which a tracking system, for example a camera tracking system, can localise the marker.

The problem to be solved by the present invention is therefore that of providing a medical navigation marker device which, by its very design, offers the highest possible tracking accuracy and in particular an improved tracking accuracy with respect to the known solutions mentioned above.

This problem is solved by the subject-matter of any appended independent claim.

Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

BRIEF EXAMPLE DESCRIPTION OF THE INVENTION

In the following section, individual aspects of the present invention are described, merely by way of example and without limiting the invention to the combination(s) of features explicitly described in this section.

In one specific example which serves to explain the invention, the medical navigation marker device is one which is to be tracked by a single video camera. It comprises a single marker carrier which comprises faces or surfaces which point in different spatial directions. Each of said surfaces features an individual marker pattern which includes a characteristic moiré pattern and also a visual code comprising dots, bars or lines, which serve as an identification pattern or identification code to enable the viewed pattern to be quickly, easily and in particular unambiguously identified by a navigation system. Because the moiré pattern offers a very high level of tracking accuracy, the combination of marker patterns allows reliable tracking, orientation information and optimum localisation accuracy to be mutually integrated.

GENERAL DESCRIPTION OF THE INVENTION

In one general aspect, the present invention relates to a medical navigation marker device comprising a light reflector which features a marker pattern having the following features:
- the marker pattern points in more than one spatial direction;
- the marker pattern comprises at least one moiré pattern which points in more than one spatial direction; and
- the marker pattern comprises a face identification pattern which identifies the face of the marker being viewed from a particular spatial direction.

In other words, a general embodiment of the marker device of the invention provides spatial orientation information combined with the ability to be highly accurately tracked, such that a marker device with a highly integrated structure which generates a corresponding synergetic effect can be provided to the user. This synergetic effect which combines tracking accuracy, directional information and an integral design is a particular advantage of the medical navigation marker device according to the present invention over any or any combination of the prior-art suggestions mentioned above, in which moiré trackers have always been conceived as flat, unidirectional devices or in which multi-directional or multi-facetted tracking devices (WO 2007/051304 A1) intended to improve and/or replace multi-directional marker spheres (DE 196 39 615 C2) have resulted in rather complicated and correspondingly expensive and difficult-to-manage structures. The present invention thus offers an integrated, easy-to-manufacture and accurate unit which provides hitherto unknown orientation information.

In this respect, it should be noted that it is highly advantageous for a person using a medical navigation system to know the direction from which the patient (with a marker device attached to them) or a patient support such as a couch (comprising a marker device) or a medical instrument (likewise comprising a marker device) is being viewed by the tracking system, in order to be able to determine a correct use or workflows or any other information which is then exactly matched to the current positional situation in the medical environment.

When embodying the marker pattern of the present invention in such a way that it points in more than one spatial direction, it is possible to choose from several options disclosed in this document. The marker pattern can for example be curved or angled (i.e. comprise multiple substantially flat surfaces arranged at an angle with respect to each other) or both curved and angled. This can be achieved by providing at least one curved face or at least two angled faces or by providing any combination of curved and angled faces. The angled faces can in particular be flat faces.

Which of the above options is chosen will depend at least in part on the application for which the marker is to be used. If, for example, it is necessary for a marker to be viewed form a range of continuously extending angles, then curved faces may be more advantageous than multiple flat surfaces arranged at particular angles with respect to each other. In applications in which the marker is only expected to be viewed from a small number of discrete angles, by contrast, the situation may be reversed, such that angled faces may be more advantageous than curved faces.

The moiré pattern can comprise at least two angled moiré fields and/or one or more curved moiré fields. As already mentioned above, the field of application will again determine which of the embodiments is the more advantageous.

One example of an angled marker pattern is an arrangement in which the light reflector is placed on or forms multiple faces of a polyhedron, in particular a tetrahedron. One example of a curved marker pattern, by contrast, is an arrangement in which the light reflector is placed on or forms a cylindrical surface. Another example of a curved marker pattern is an arrangement in which the light reflector is placed on or forms a spherical surface.

The light reflector could be formed simply by using the marker elements itself, such as for example in the form of foils which form or form part of the marker elements. In one embodiment, however, the medical marker device according to the invention can be realised by arranging the marker pattern on a marker carrier, thus providing the unit as a whole with a certain stability. However, it is also conceivable to provide a stable and/or rigid marker carrier and simply adapt, finish or machine the marker pattern into its surface. Etching or laser ablation techniques could for example be used for this purpose.

In accordance with one advantageous embodiment, the medical marker device forms a single, spatially located marker element which consists of the light reflector and, if provided, the marker carrier.

One of the most important advantages of the marker device according to the present invention is that it can be formed as a single element and need not form an arrangement of elements as is generally the case in the prior art. Its multi-directionality (due to the marker pattern which points in more than one spatial direction and the multiple identification patterns which identify the respective face which is viewed from a particular spatial direction) and the outstanding level of accuracy provided by a moiré tracking pattern allow the marker device to be embodied as a single element. In this highly integrated form, the marker device of the present invention demonstrates great practicability, since it can be seen and accurately tracked from any direction but is not space-consuming and need not obstruct the personnel working in the medical environment. Moreover, such highly integrated single marker elements can be easily and effectively adapted to individual applications, in particular in environments such as operating theatres in which it is necessary to maintain sterility.

The face identification pattern needs to be easy for a logic or software to identify on the basis of the visual information which the face identification pattern provides and the logic or software analyses. To this end, the face identification pattern can comprise one or more and/or any combination of:
  a characteristic array of
    dots or
    single or multiple lines or
    simple forms such as rings or polygons or
    straight bars or curved bars which in particular exhibit different colours and/or levels of brightness;
  bar codes or QR codes or a characteristic array of the same;
  grids or crosshairs;
  numerical digits.

These and/or similar graphical elements enable the viewing direction to be quickly and reliably determined. Within this context, but also with respect to the present disclosure as a whole, it should be noted that the expression "face" or "face of the marker" may relate not only to a flat surface but also to a particular, (very) small or somewhat wider area of a curved face which points in and/or is viewed from one direction. In the case of a spherical marker, this face could be the complete or partial circle which a sphere presents to a viewer or viewing device.

The angles between the spatial directions in which the marker pattern points or, in other words, the angles between the spatial directions from which the marker can be effectively viewed, can total between 60 and 360° in at least one viewing plane. As mentioned above, it may be clear and/or known in particular applications that the marker will only be viewed from a couple of directions which do not significantly differ from each other, in which case the sum of the angles will be small and the design of the marker can be adapted accordingly. In other applications, it may be necessary to view the marker from almost every direction, in which case the sum of the angles will approach or reach 360°, for which the marker design must again be adapted accordingly.

In accordance with one embodiment of the medical marker device according to the present invention, the light reflector reflects light in the visible spectrum which can be detected by a video camera.

In accordance with another aspect, the present invention relates to a combination of a medical marker device as described in this document in various embodiments and a medical navigation system which uses the marker device as a spatial position and/or orientation marker or "tracking marker", wherein these terms can be used synonymously.

A navigation system for computer-assisted surgery can be defined in general terms as comprising a computer for processing data and a detection device (such as for example a camera) for detecting the position of tracking markers in order to generate detection signals and supply the generated detection signals to the computer, such that the computer can determine positional information on the basis of the detection signals received. The navigation system also preferably comprises a user interface for receiving the calculation results from the computer. The user interface provides received and/or determined data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer. Navigation systems which can be used with the present invention include those described in DE 196 39 615 C2 or EP 2 179 703 B1, the content of which relating to the design and structure of the navigation system is hereby incorporated by reference.

In accordance with yet another aspect, the present invention relates to the use of a medical marker device, such as is described in this document in several embodiments, for providing guidance to a user of a medical navigation system by evaluating the spatial position and/or orientation information provided by the marker device.

This use can comprise one or more of the following actions to be taken on the basis of the evaluation of the information:

- adapting the clinical logic in response to marker tracking or marker localising information;
- activating medical devices, in particular playing back videos on a display;
- initiating workflows or certain parts of workflows, in particular by providing visual or acoustic assistance and/or instructions;
- updating navigation and tracking calculations and/or procedures if a tracked device has moved and/or changed its orientation, in particular if a patient support has been moved or rotated.

The action of "adapting the clinical logic" can refer to a number of procedures, including (but not restricted to) the following:

- the identification information regarding the marker, in particular the face identification pattern, encodes the type of interaction presently being performed and guided by the navigation system (for example image acquisition, patient registration, patient positioning, etc.);
- the type of data shown to the user is encoded or selected on the basis of information which describes the direction from which a marker is being viewed by a camera or user, wherein for example the varus/valgus angle is shown if the camera or user is viewing a tibia from the front, or the anterior/posterior slope angle is shown if the camera or user is viewing the tibia from the side;
- the current orientation of the patient is determined, for example by determining the face of the marker presently being viewed, in order to determine whether a patient couch or patient table has been rotated by a certain amount (for example 90°, either for an intra-operative CT scan or for patient access).

The invention does not involve or in particular comprise or encompass an invasive step which would represent a substantial physical interference with the body requiring professional medical expertise to be carried out and entailing a substantial health risk even when carried out with the required professional care and expertise. In particular, the invention does not comprise a step of connecting/implanting a medical device to/into an anatomical structure or a step of preparing the anatomical structure to receive the medical implant to be connected/implanted. In particular, the invention does not involve or in particular comprise or encompass any surgical or therapeutic activity. No surgical or therapeutic activity and in particular no surgical or therapeutic step is necessitated or implied by carrying out the invention.

DESCRIPTION OF THE FIGURES

In the following, the invention is described with reference to the appended figures, without being limited to the features and combinations of features explicitly described in relation to and illustrated by the figures.

Figure 1:
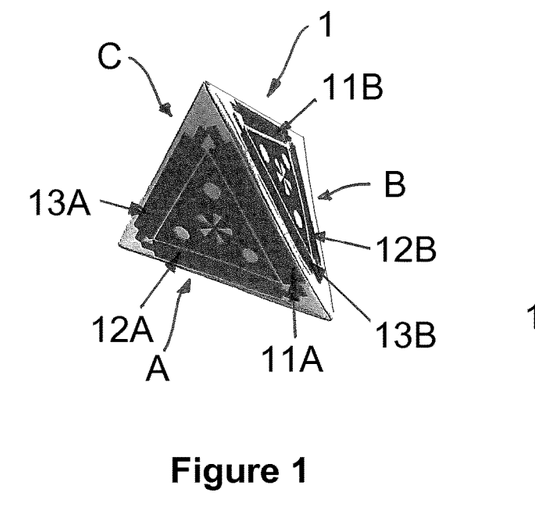
FIG. 1 shows a perspective view of a medical marker device in accordance with a first embodiment of the invention, in the form of a tetrahedron.

A first embodiment of the medical marker device according to the present invention is illustrated in FIGS. 1 to 4. FIG. 1 shows that the marker device 1 is shaped as a tetrahedron, of which however only the faces A and B are visible in FIG. 1. Face C is situated on the rear side and is designed in a similar manner to faces A and B. Fastening means can be provided on the remaining fourth side which is not indicated by a reference sign.

Each of the faces A, B and C has a marker pattern. In FIG. 1, three moiré fields are shown on each of the faces A and B and indicated by the reference numerals 11, 12 and 13, with the letter A or B appended in each case to denote the respective face. Though not visible in FIG. 1, the face C features the same marker pattern as the faces A and B. The three moiré fields 11, 12 and 13 on each of the faces A, B and C form the three sides of an outer triangle and exhibit a particular width Within this outer triangle, another triangular moiré field is provided on each of the faces A, B and C, which contains white dots serving as an identification pattern. For reasons of presentation, the inner triangular moiré field and the identification patterns have not been provided with separate reference numerals.

Figure 2:
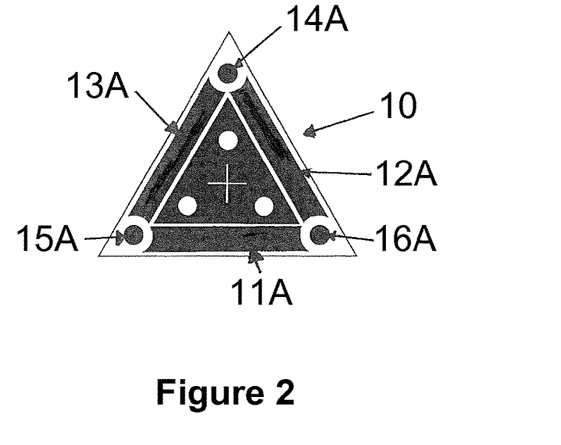
FIGS. 2 and 3 show details of the marker device of FIG. 1.
Figure 3:
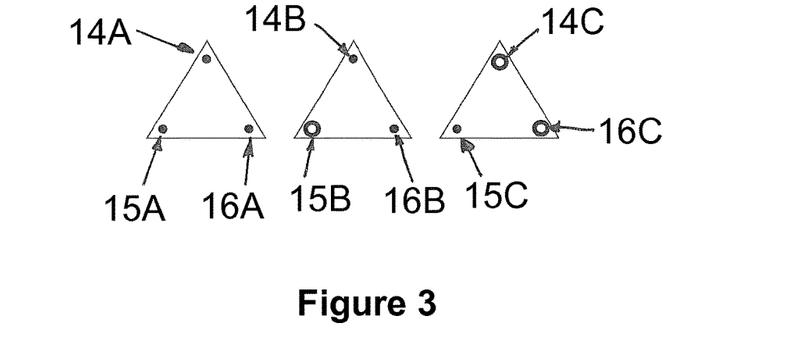

Another possible design of the faces is shown in FIGS. 2 and 3 (in FIG. 2, by way of the example of the face A only). The faces are again referred to as A, B and C, and the reference numerals which indicate the moiré fields are again appended with the letters A, B and C to denote the face on which the fields are presented.

The face A in FIG. 2 features three moiré strips 11A, 12A and 13A which form an outer triangle, and an inner triangular moiré field which additionally comprises three white dots and a white cross which can serve as an identification pattern (identification code) for the face A together with the identification dots 14A, 15A and 16A at the respective corners of the triangle.

A particular effect generated by the moiré patterns is used to exactly determine the direction from which the moiré field and therefore the marker device is being viewed, for example by a video camera. This directional information enables a highly accurate positional localisation of the marker by means of a tracking/navigation system.

Specifically, moiré patterns can be used which consist of secondary and visually evident superimposed patterns, as for example when two identical, usually transparent patterns on a surface (such as closely spaced straight lines drawn radiating from a point or taking the form of a grid) are overlaid while displaced or rotated a small amount from one another. A moiré pattern can therefore also be defined as a pattern formed by overlaid geometrical structures such as lines or grids. Straight or curved geometrical structures can be used, and the overlaid patterns can be rotated or merely shifted with respect to one another. Because one pattern overlays the other, the moiré field looks different when viewed from different directions and generates characteristic optical impressions such as overlay patterns which are larger in size than the individual moiré structures themselves. On the basis of these effects, the viewing direction and therefore the location or position of a moiré field or a marker having a moiré field can be optically detected to a very high level of accuracy.

Thus, the moiré patterns provide detailed viewing direction information, while the face identification patterns provide general viewing direction information.

The aspect of face encoding or face identification provided by the marker devices according to the present invention can best be explained by referring to FIG. 3 which shows the three sides A, B and C of the marker device 1 in isolation, as well as the face identification markers 14, 15 and 16 at the corners of each triangular face. The markers 14A, 15A and 16A on the face A are all dots, while the markers on the face B include one ring-shaped marker 15B and two dots 14B and 16B, and the markers on the face C include two ring-like markers 14C and 16C and one dot 15C. An image recognition software can very easily and quickly determine, from a received image of one of the sides A, B or C, which of these sides is presently being viewed by the camera, and on the basis of this information alone, a medical navigation software can provide data which a user would need in this situation and which are characterised by the spatial orientation of the marker device. By determining the orientation of the marker device by means of the face identification markers 14, 15 and 16, the system would for example be able to determine whether a patient couch was still in a preparatory position or had already been moved (rotated) into a position in which to be imaged by an imaging unit such as a CT scanner, and a user could then be provided with the respective matching images or a workflow on a display.

Figure 4:
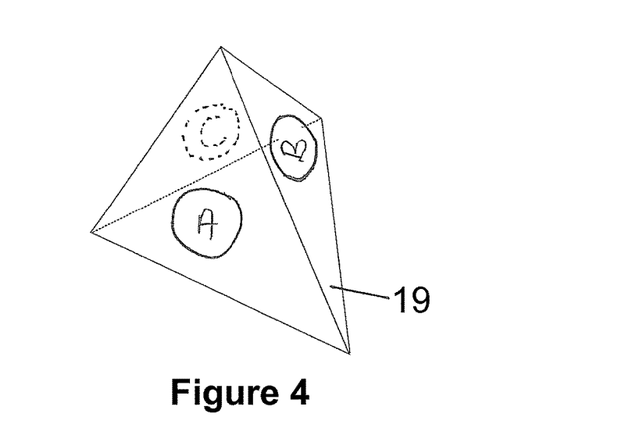
FIG. 4 shows a marker carrier of the marker device of FIG. 1.

FIG. 4 very clearly shows the tetrahedral shape of the marker device according to this example embodiment, in that it shows a schematic and transparent representation of the marker carrier 19 and its sides A, B and C. The marker patterns shown in FIGS. 1 to 3 could be fastened to the faces A, B and C, to create a complete marker device in accordance with the present invention.

Figure 5:
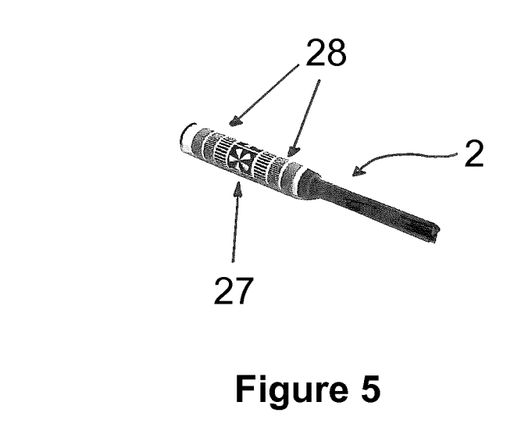
FIGS. 5 to 7 show a perspective view, detail and marker carrier, respectively, of a second embodiment of the medical marker device according to the invention, in the form of a cylinder.
Figure 6:
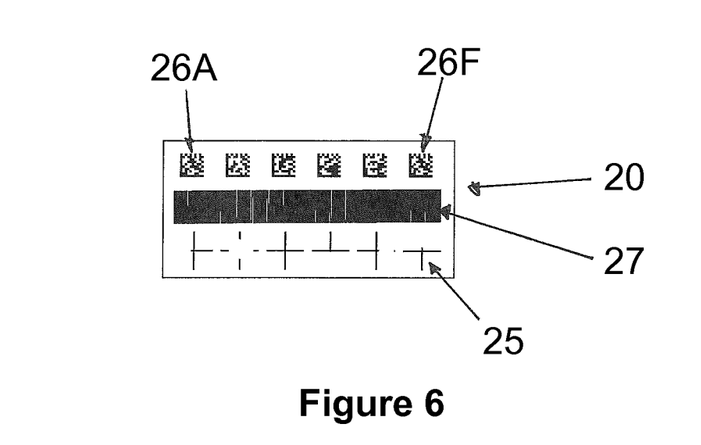
Figure 7:
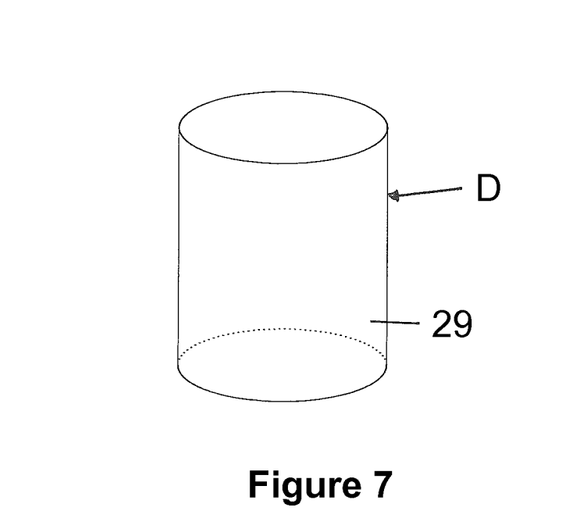

A second embodiment of a marker device in accordance with the present invention is illustrated in FIGS. 5 to 7. In the perspective view shown in FIG. 5, it can be seen that the cylindrical marker device 2 has a moiré pattern 27 and a face identification pattern 28 which in this example is embodied as a pattern of bars or lines. In this example embodiment, the moiré pattern 27 is curved and comprises several individual fields, wherein the curvature represents an additional characteristic of the pattern which the overlaid moiré layers will present from any given viewing direction.

The general viewing direction can in turn be easily identified on the basis of the characteristics which the face identification pattern 28 exhibits when viewed from any given viewing direction. In this respect, it could also be said that the face identification pattern 28 "encodes" the face of the marker device as viewed from a particular viewing direction, such that the face identification pattern could also be referred to as a "face encoding" pattern. This consideration as well as the general considerations regarding marker localisation by moiré patterns and face identification as set forth with respect to the first embodiment, can of course apply to any or all of the embodiments or marker devices in accordance with the present invention.

FIG. 6 shows an example of a foil or strip 20 which can be fastened to the surface of a cylindrical marker carrier 29 (shown in FIG. 7) and the middle of which comprises a moiré pattern 27. This moiré pattern 27 is an overlaid line pattern which is formed as a strip of a certain width and flanked on either side by face identification patterns or face codes 25 and 26. The upper face codes are QR codes 26A to 26F, while the lower face codes are complete or incomplete crosshairs 25.

Figure 8:
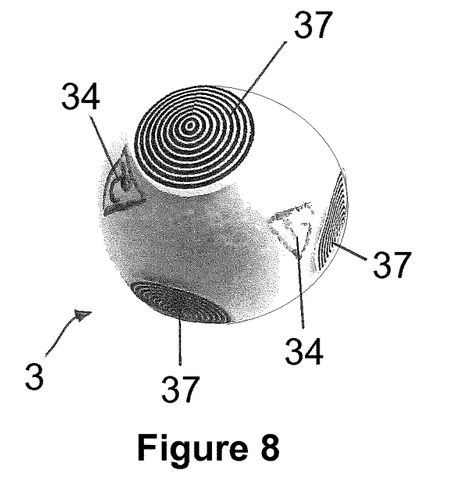
FIGS. 8 to 11 show a perspective view, detail and marker carrier, respectively, of a third embodiment of the medical marker device in accordance with the invention, in the form of a sphere.
Figure 9:
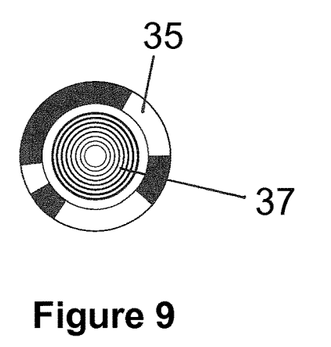
Figure 10:
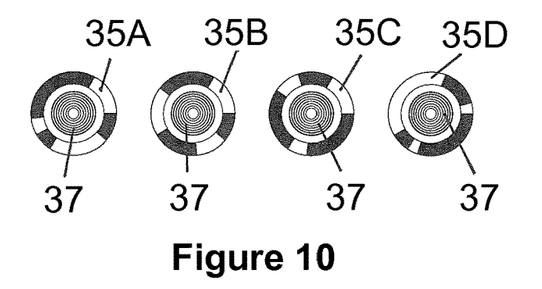
Figure 11:
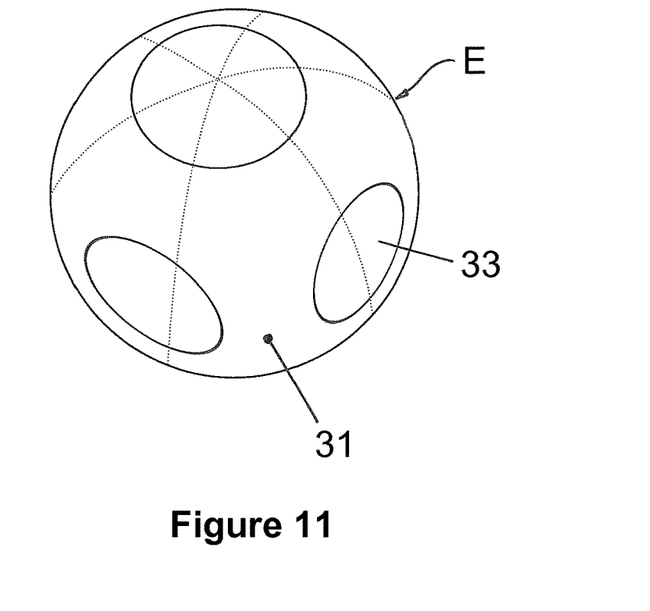

A third embodiment of a medical marker device according to the present invention is shown in FIGS. 8 to 11. FIGS. 8 and 11 show a perspective view of a spherical marker device 3 and its marker carrier 31, respectively. Face identification patterns 34 (in the form of numerical digits in the example shown) and moiré patterns 37 are displayed. Both the face identification patterns and the moiré patterns are disposed at assigned regions (indicated by 33 in FIG. 11) on the surface E of the marker carrier and are preferably distributed equidistantly on the surface E and in such a way that the viewing direction can be positively identified and a majority portion of the moiré fields can be viewed from any viewing angle.

The position is determined using the moiré fields 37 and the viewing direction is determined using the face identification patterns 34 in the way already explained above.

FIGS. 9 and 10 show one way of combining the moiré fields 37 and the face identification patterns 35, by encircling the circular moiré fields 37 with a ring of black and white portions, wherein the white portions vary between each combination of a ring and a moiré field. These variations are illustrated by the respective white portions 35A, 35B, 35C and 35D as shown in FIG. 10.

Though shown in combination in FIGS. 9 and 10, the moiré fields 37 and the face identification rings 35 can of course also be used in isolation.

Figure 12:
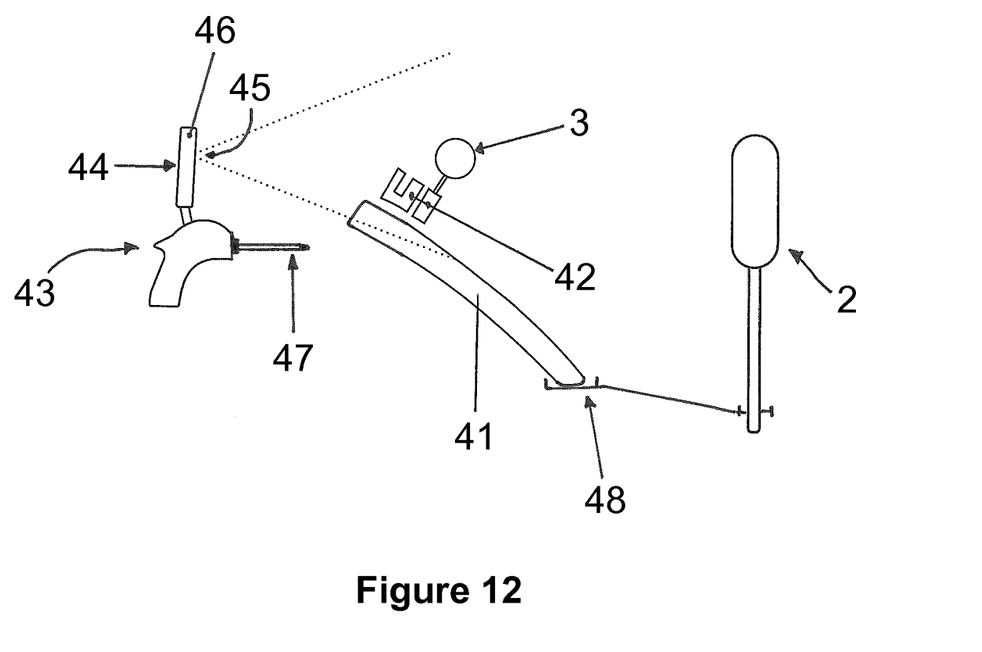
FIG. 12 schematically shows how marker devices in accordance with the invention can be integrated into and used with a navigation system.

FIG. 12 schematically shows medical navigation marker devices in accordance with the present invention being used in the environment of a medical navigation (and tracking) system. The navigation system has been provided with the reference numeral 43 and is a hand-held navigation system comprising a combined unit 46 which accommodates the computational unit and logic as well as a display 44 and a video camera 45. The handle of the navigation system comprises a pointer 47 which could for example be used for the purpose of navigational registration.

The navigation system determines the spatial positions and positional relationships of medical apparatus or parts of the patient's body, and the reference numeral 41 denotes a schematic representation of one of these elements. A schematically represented medical device 42, for example a spherical marker device 3 as shown in FIGS. 8 to 11, is attached to the element 41 which is to be positionally determined and/or tracked. The element 41 is also supported by a bearing support 48 which itself bears a marker device 2, for example a cylindrical marker device as shown in FIGS. 5 to 7. For reasons of clearer depiction, the relative proportions in the schematic representation of FIG. 12 may be outside the strictly realistic range.

The navigation system 43 views the marker devices 2 and 3 using the camera 45. The computational unit then determines the face (specifically, the cylinder segment in the case of the marker device 2 or the spherical sector in the case of the marker device 3) which is currently orientated towards the camera 45 by identifying the face identification patterns on the marker devices 2 and 3. On the basis of this information, a matching workflow or matching imaging data which is/are always correctly adapted to the current positional situation as defined by the spatial orientation of the marker devices 2 and 3 can be shown on the display 44 of the navigation system 43.

On the other hand, the position of the marker devices 2 and 3 is determined to a high degree of accuracy in a second step by using the moiré patterns on the marker devices, thereby obtaining information about the spatial position of the device 42, the support 48 and the element 41, wherein this positional information can be used to provide navigational guidance to the user. Such navigational guidance can also be displayed on the display 44 and could, in one example, aid in correctly registering landmarks in order to register the element 41 in the spatial environment of the navigation system 43 by means of the registration pointer 47.

The steps of face identification and accurate moiré localisation can of course also be performed simultaneously or in any order other than that explained by way of example above, in particular where such a different order would better suit the current application.

The invention claimed is:

1. A medical navigation marker device comprising a light reflector featuring a marker pattern comprising an integration of a face identification pattern and a detailed direction pattern, wherein:
   the marker pattern points in multiple non-parallel spatial directions by comprising at least two non-parallel angled faces;
   the face identification pattern is configured to provide information identifying a particular face of the medical navigation marker device viewable from a particular spatial direction; and
   the detailed direction pattern is configured to provide spatial orientation information for the medical navigation marker device, the detailed direction pattern being integrated with the face identification pattern and comprising at least two angled moiré fields that are configured to generate at least one moiré pattern that points in multiple non-parallel spatial directions.

2. The medical navigation marker device according to claim 1, wherein the marker pattern is arranged on or forms multiple faces of a polyhedron.

3. The medical navigation marker device according to claim 2, wherein the polyhedron is a tetrahedron.

4. The medical navigation marker device according to claim 1, wherein the light reflector is arranged on or forms a marker carrier.

5. The medical navigation marker device according to claim 1, wherein the medical navigation marker device forms a single, spatially located marker element that consists of the light reflector and a marker carrier.

6. The medical navigation marker device according to claim 1, wherein the angles between the multiple non-parallel spatial directions in which the marker pattern points total between 60 and 360° in at least one viewing plane.

7. The medical navigation marker device according to claim 1, wherein the light reflector is configured to reflect light in the visible spectrum that can be detected by a video camera.

8. A method comprising:
   attaching a medical navigation marker device to a target element, the medical navigation marker device comprising a light reflector featuring a marker pattern comprising an integration of a face identification pattern and a detailed direction pattern, wherein:
      the marker pattern points in multiple non-parallel spatial directions by comprising at least two non-parallel angled faces;
      the face identification pattern is configured to provide information identifying a particular face of the medical navigation marker device viewable from a particular spatial direction; and
      the detailed direction pattern is configured to provide spatial orientation information for the medical navigation marker device, the detailed direction pattern being integrated with the face identification pattern and comprising at least two angled moiré fields that are configured to generate at least one moiré pattern that points in multiple non-parallel spatial directions;
   determining, by the medical navigation system, the particular face of the medical navigation marker device facing a camera of the medical navigation system using the face identification pattern of the medical navigation marker device;
   determining, by the medical navigation system, a spatial position or orientation of the medical navigation maker device using the detailed direction pattern of the medical navigation marker device;
   providing guidance, by the medical navigation system, to an associated user of the medical navigation system by evaluating the determined particular face of the medical navigation marker device facing the camera of the medical navigation system or the determined spatial position or orientation of the medical navigation marker device.

9. The method according to claim 8, wherein at least one of the following actions are taken on the basis of the guidance provided by the medical navigation system:
   adapting clinical logic in response to marker tracking or marker localising information;
   activating medical devices;
   initiating workflows or certain parts of workflows; or
   updating navigation and tracking calculations or procedures in a condition that the medical navigation marker device has moved or changed its orientation.

10. The method according to claim 9, wherein adapting the clinical logic comprises at least one of the following procedures:
   encoding, based on the marker tracking or the marker localising information, a type of interaction presently being performed and guided by the medical navigation system;
   encoding or selecting a type of data shown to the associated user on the basis of information that describes a direction from which the medical navigation marker device is being viewed by the camera or the associated user;
   determining a current orientation of the patient.

11. The method according to claim 9, wherein the activating medical devices includes playing back videos on a display.

12. A system comprising:
   a medical navigation marker device comprising a light reflector featuring a marker pattern comprising an integration of a face identification pattern and a detailed direction pattern, wherein:
      the marker pattern points in multiple non-parallel spatial directions by comprising at least two non-parallel angled faces;
      the face identification pattern is configured to provide information identifying a particular face of the medical navigation marker device viewable from a particular spatial direction; and
      the detailed direction pattern is configured to provide spatial orientation information for the medical navigation marker device, the detailed direction pattern being integrated with the face identification pattern and comprising at least two angled moiré fields that are configured to generate at least one moiré pattern that points in multiple non-parallel spatial directions; and a medical navigation system configured to determine a spatial position or an orientation of the medical navigation marker device based on information provided from the face identification pattern and the detailed direction pattern.

* * * * *